US008517608B1

(12) United States Patent
Arnold

(10) Patent No.: US 8,517,608 B1
(45) Date of Patent: Aug. 27, 2013

(54) SYSTEM AND METHOD FOR CALIBRATION OF CT SCANNERS AND DISPLAY OF IMAGES IN DENSITY UNITS WITHOUT THE USE OF WATER PHANTOMS

(76) Inventor: Ben A. Arnold, Columbia, KY (US)

(*) Notice: Subject to any disclaimer, the term of this patent is extended or adjusted under 35 U.S.C. 154(b) by 0 days.

(21) Appl. No.: 13/566,918

(22) Filed: Aug. 3, 2012

Related U.S. Application Data

(60) Provisional application No. 61/514,888, filed on Aug. 3, 2011.

(51) Int. Cl.
*G01D 18/00* (2006.01)

(52) U.S. Cl.
USPC .......................................................... 378/207

(58) Field of Classification Search
USPC .................................. 378/207; 382/128–131
See application file for complete search history.

(56) References Cited

U.S. PATENT DOCUMENTS

| 3,778,614 | A | 12/1973 | Hounsfield |
| 4,233,507 | A | 11/1980 | Volz |
| 4,649,561 | A | 3/1987 | Arnold |
| 4,663,772 | A | 5/1987 | Mattson et al. |
| 4,724,110 | A | 2/1988 | Arnold |
| 4,782,502 | A | 11/1988 | Schulz |
| 4,870,666 | A | 9/1989 | Lonn et al. |
| 4,922,915 | A | 5/1990 | Arnold et al. |
| 4,985,906 | A | 1/1991 | Arnold |
| 5,034,969 | A | 7/1991 | Ozaki |
| 5,068,788 | A | 11/1991 | Goodenough et al. |
| 5,222,021 | A | 6/1993 | Feldman et al. |
| 5,235,628 | A | 8/1993 | Kalender |
| 5,335,260 | A | 8/1994 | Arnold |
| 5,442,674 | A | 8/1995 | Picard et al. |
| 5,521,955 | A | 5/1996 | Gohno et al. |
| 5,577,089 | A | 11/1996 | Mazess |
| 5,696,805 | A | 12/1997 | Gaborski et al. |
| 5,712,892 | A | 1/1998 | Weil et al. |
| 5,757,877 | A | 5/1998 | Wilting |
| 5,774,519 | A | 6/1998 | Lindstrom et al. |
| 5,782,762 | A | 7/1998 | Vining |
| 5,891,030 | A | 4/1999 | Johnson et al. |
| 6,026,142 | A | 2/2000 | Gueziec et al. |
| 6,226,350 | B1 | 5/2001 | Hsieh |
| 6,233,304 | B1 | 5/2001 | Hu et al. |
| 6,243,437 | B1 | 6/2001 | Hu et al. |

(Continued)

OTHER PUBLICATIONS

Agatston, Arthur S. et al. Quantification of coronary artery calcium using ultrafast computed tomography, American College of Cardiology, 1990; 15: pp. 827-832.

(Continued)

*Primary Examiner* — Courtney Thomas
(74) *Attorney, Agent, or Firm* — Jerry Turner Sewell

(57) ABSTRACT

A system and method enable calibration of CT scanners without using water phantoms. Tissue densities are expressed in either the Hounsfield Scale units (HU) referenced back to water or the proposed Gram Scale units (GU) with voxel intensities expressed in true density units. The fully automatic software-only method requires no interactions with the images. Routine calibration of CT scanners with water phantoms can be eliminated. The method further provides accurate calibrations that are patient, scanner, and scan specific and are repeatable over long time durations. The calibrations are based on the uniquely defined intensity of voxels with equal contributions of two tissues types. This calibration point is immune to the many variables found in ROI histogram measurements of mean, mode, SD or other measures of voxel intensities. The disclosed CT scanner system provides consistent CT image voxel intensities of the various tissues across a great variety of patients.

29 Claims, 10 Drawing Sheets

(56) References Cited

U.S. PATENT DOCUMENTS

| | | |
|---|---|---|
| 6,278,761 B1 | 8/2001 | Kim et al. |
| 6,302,582 B1 | 10/2001 | Nord et al. |
| 6,320,931 B1 | 11/2001 | Arnold |
| 6,421,552 B1 | 7/2002 | Hsieh |
| 6,438,403 B1 | 8/2002 | Cline et al. |
| 6,625,303 B1 | 9/2003 | Young et al. |
| 6,639,965 B1 | 10/2003 | Hsieh et al. |
| 6,674,834 B1 | 1/2004 | Acharya et al. |
| 6,697,451 B2 | 2/2004 | Acharya et al. |
| 6,708,055 B2 | 3/2004 | Geisser et al. |
| 6,789,943 B2 | 9/2004 | Zapalac |
| 6,990,222 B2 | 1/2006 | Arnold |
| 7,127,096 B2 | 10/2006 | Kaufman et al. |
| 7,203,354 B2 | 4/2007 | Wilson et al. |
| 7,251,306 B2 | 7/2007 | Sauer et al. |
| 7,409,035 B2 | 8/2008 | Kaufman et al. |
| 7,471,765 B2 | 12/2008 | Jaffray et al. |
| 7,558,611 B2 | 7/2009 | Arnold et al. |
| 7,583,778 B2 | 9/2009 | Mori |
| 7,970,196 B2 | 6/2011 | Arnold et al. |
| 8,139,836 B2 | 3/2012 | Arnold et al. |
| 8,186,880 B1 | 5/2012 | Arnold |
| 2003/0048867 A1 | 3/2003 | Acharya et al. |
| 2003/0095693 A1 | 5/2003 | Kaufman et al. |
| 2003/0120134 A1 | 6/2003 | Rao et al. |
| 2007/0116345 A1 | 5/2007 | Peterson et al. |
| 2008/0273652 A1 | 11/2008 | Arnold et al. |
| 2009/0136107 A1 | 5/2009 | Arnold et al. |
| 2010/0012845 A1 | 1/2010 | Baeumer et al. |

OTHER PUBLICATIONS

Baldy, R.E. et al., A Fully-Automated Computer Assisted Method of CT Brain Scan Analysis for the Measurement of Cerbrospinal Fluid Spaces and Brain Absorption Density, Neuroradiology, vol. 28, 1986, pp. 109-117.

Brown, Matthew S. et al., Knowledge-based segmentation of thoracic computed tomography images for assessment of split lung function, Medical Physics, vol. 27, No. 3, Mar. 2000, pp. 592-598.

Grashuis, J.L. et al., Semi-Automatic Contour Detection in CT-Scans of the Lumbar Spine, Proceedings of the Sixth International Workshop on Bone and Soft Tissue Densitometry, Buxton, England, Sep. 22-25, 1987, p. 33.

Greaser, L.E. 3rd et al., Electron-beam CT: the effect of using a correction function on coronary artery calcium quantitation, Acad. Radiol., vol. 6, No. 1, Jan. 1999, pp. 40-48. (one-page abstract).

Heil, Robert H., Jr., et al., Quantitative Materials Evaluation and Inspection with the Image Analysing Computer, Proceedings of the Society of Photo-Optical Instrumentation Engineers, Feb. 1972, pp. 131-143.

Kachelreiss, Marc et al., ECG-correlated image reconstruction from subsecond multi-slice spiral CT scans of the heart, American Institute of Medical Physics, vol. 27, No. 8, Aug. 2000, pp. 1881-1902.

Kalender, Willi A. et al., Vertebral Bone Mineral Analysis: An Integrated Approach with CT, Radiology, 1987, vol. 164, No. 2, Aug. 1987. pp. 419-423.

Kalender, W.A. et al., Methodological Aspects of Bone Mineral Measurements by QCT: Minimizing Operator Influence on Reproducibility, Proceedings of the Sixth International Workshop on bone and Soft Tissue Densitometry, Buxton, England, Sep. 22-25, 1987, p. 31.

Keller, James M. et al., Automatic Outlining of Regions on CT Scans, Journal of Computer Assisted Tomography, vol. 5, No. 2, Apr. 1981, pp. 240-245.

Kemerink, G.J. et al., Scanner conformity in CT densitometry of the lungs, Radiology, vol. 197, No. 3, Dec. 1995, pp. 749-752. (one-page abstract).

McCullough, Cynthia H., Ph.D., Electron-Beam CT: Use of a Calibration Phantom to Reduce Variability in Calcium Quntitation, Departments of Diagnostic Radiology and Physiology and Biophysics, Mayo Clinic and Mayo Foundation, Rochester, Minnesota, vol. 196, No. 1, Jul. 1995, pp. 159-165.

Reed, Judd E. et al., System for Quantitative Analysis of Coronary Calcification via Electron Beam Computed Tomography, Medical Imaging 1994, Physiological and Function from Multidimensional Images, SPIE, vol. 2168, Feb. 13-14, 1994, pp. 43-53.

Stoel, B.C. et al., Sources of error in lung densitometry with CT, Invest. Radiol., vol. 34, No. 4, Apr. 1999, pp. 303-309. (one-page abstract).

Wankling, P.F. et al., Computer Recognition Applied to C.T. Scans for the Automation of the Procedure for Bone Mineral Measurement Allowing Consistent Measurement Without Operator Intervention, Proceedings of the Sixth International Workshop on Bone and Soft Tissue Densitometry, Buxton, England, Sep. 22-25, 1987, p. 32.

Yoon, H.C. et al., Coronary artery calcium: alternate methods for accurate and reproducible quantitation, Acad. Radiol., vol. 4, No. 10, Oct. 1997, pp. 666-673. (one-page abstract).

General Electric, Marketing Materials distributed in 1987, four pages.

Technical Note, Automatic Outlining Technique for EMI Scanner Pictures, Medical & Biological Engineering & Computing, vol. 17, Sep. 1979, pp. 693-694.

The Gram Scale

|  | Air | Fat | Body Water | Water | Muscle | Bone |
|---|---|---|---|---|---|---|
| HU Scale | -1000 | -100 |  | 0 | 55 | 3000 |
| Density | 0 | 0.901 | 0.994 | 1 | 1.047 | 1.85 |
| GU Scale | -1000 | -100 | -6 | 0 | 47 | 1850 |

FIG. 11

The Gram Scale

| HU Scale | -1000 |  | 0 |  | 3000 |
|---|---|---|---|---|---|
|  |  | STR ↓ |  |  |  |
| GU Scale | -1000 | -26 | 0 |  | 1850 |

Density (mg/cc) = 1000 + GU

FIG. 12

SYSTEM AND METHOD FOR CALIBRATION OF CT SCANNERS AND DISPLAY OF IMAGES IN DENSITY UNITS WITHOUT THE USE OF WATER PHANTOMS

RELATED APPLICATIONS

The present application claims the benefit of priority under 35 USC §119(e) to U.S. Provisional Application No. 61/514,888, filed on Aug. 3, 2011, which is incorporated by reference herein.

BACKGROUND OF THE INVENTION

1. Field of the Invention

The present invention is in the field of 3-D volumetric medical imaging, and, in particular, is directed to an improved system and method to calibrate the images of CT scanners.

2. Description of the Related Art

The original Hounsfield patent, disclosing the first CT scanner in 1973, used water as reference material (Hounsfield, U.S. Pat. No. 3,778,614). All of CT since has been based on water as reference calibration material and lead to the Hounsfield Scale (HU units) in honor of Hounsfield for this most important and Noble Prize winning invention. CT scanners continue to be calibrated to this day with water equivalent phantoms, typically circular solid or liquid water filled cylinders. Such calibrations are essential to CT scanner use in medical imaging and require routine re-calibrations by periodically scanning such phantoms. This requires significant time and effort to determine and continue to maintain scanners within relatively narrow calibration ranges, even for the idealized water phantoms (on the order of +/-3 HU units). The resulting pixel intensities of clinical images are therefore approximately representative of the underlying tissue densities and atomic numbers and provide spectacular images for subjective viewing and diagnosis. However, the pixel values are sufficiently inaccurate and carry significant variability to limit their use in a variety of clinical applications. More accurate and reproducible measurements of the densities of almost all tissues and organ systems of the body have potential clinical value and have long been a goal of the medical imaging industry.

The fundamental limitation of calibration with idealized water cylinders is the inability to accurately simulate the great variability of the human body in terms of size, shape, and composition. The resulting images are not adequately representative of the underlying tissues for individual patients or from scanner to scanner.

These historic limitations of water calibrations have been made much worse with the availability of the more recent multi-detector CT scanners (MDCT) with 64 to 256 detector rows. The increased volume of tissue imaged in each rotation leads to greatly increased scattered radiation at the detectors. One of the advantages of earlier single slice scanners was the resulting avoidance of scatter due to the narrow beam conditions. Indeed the scatter component from single slice scanners was only a few percent of the primary beam. With current MDCT scanners, the scatter can be greater than the primary beam resulting in the requirement that manufacturers use various scatter correction methods to improve the images and remove artifacts. The MDCT images provide much faster scan times allowing cardiac studies and excellent images for viewing. However, the high scatter degrades the MDCT images and leads to greater errors in the HU values. This problem is made even worse by the methods used by the manufacturers to correct for the scatter effects. These corrections, mainly consisting of differing combinations of three methods, are proprietary, differ with manufacturers, create variable and larger errors in HU values, and are not sufficiently specific for individual patients. As a result, the reliability of CT HU values for MDCT scanners has become significantly worse.

There are now several clinical applications that require conversion of the customary HU scale of CT images to density units. This requires additional calibrations with added time and costs. There are therefore advantages to presenting CT images directly in density units instead of the HU units.

Early efforts to measure tissue densities focused on so-called 'hard tissue' namely bone. Since bone contains calcium as the primary component, CT scanner HU units were particularly inaccurate because of the increased energy dependence of x-ray attenuation in higher z materials and the variable attenuation in different body regions and bodies of different sizes and compositions. In order to overcome this energy dependence and obtain accurate calibrations, external bone equivalent phantoms have been scanned simultaneously with the patient in bone densitometry (see, for example, U.S. Pat. No. 4,233,507 to Volz; and U.S. Pat. No. 4,922,915 to Arnold). Such phantoms and methods have more recently been applied to calibration of vascular calcifications (see, U.S. Pat. No. 7,558,611 to Arnold). For any tissue which has a significant energy dependent x-ray attenuation in the diagnostic energy range, such calibrations are advantageous and the attenuation properties of the target tissue and the reference calibration phantom must be sufficiently close to allow accurate calibrations. Such methods have been extended to calibration of tissue iodine contrast media density by the similar use of phantoms with iodine reference materials (see, U.S. Pat. No. 8,186,880 to Arnold). In an effort to further improve upon these methods, Arnold disclosed methods that use both external phantoms and internal tissues for a so-called "hybrid" calibration method (see, U.S. Pat. No. 6,990,222). This method has several advantages for calibration of higher atomic number targets and tissues.

A prior art method to calibrate CT scanners without phantoms for bone density measurements was disclosed by Goodenough (see, U.S. Pat. No. 5,068,788). This method uses region-of-interest (ROI) measurements of muscle regions and fat regions to estimate a calibration relationship for bone. The reference regions, namely fat and muscle ROIs, do not have the same energy dependent x-ray attenuations as bone, and required an undisclosed, empirical method to develop a relationship of bone to muscle and fat. The Goodenough and here disclosed methods are similar in that both measure parameters from the histograms of muscle and fat in CT images and compute the density of another tissue. The Goodenough method however requires an operator to manually place the ROIs at specific locations to include fat or muscle in each image to be calibrated and so the method is not automatic. Goodenough did not disclose methods for water calibration of CT scanners or calibration of the displayed images to a density scale.

SUMMARY OF THE INVENTION

There is therefore a need not met with the prior art methods for improved ways to calibrate CT scanners for tissue densities without the added work and costs of water phantom calibrations. There is also a need to find improved calibrations that are more accurate and specific for each patient, scan, and scanner. The idealized circular and homogeneous water phantoms do not accurately represent specific patient sizes, shapes or compositions. There is also the need to carry out these calibration in background mode with automated software to avoid the time and cost of operator interactions and manual placements of ROIs. There are advantages in computing CT images in density units as a replacement for the water based HU units. It is desirable that such density-based images are presented for routine viewing with a subjective appearance not distractible or readily distinguishable from current methods.

The calibration need for which the disclosure herein presents a solution is further defined to include standardization among CT scanners, beam energies and scan parameters, and to serve as a universal standard.

Methods are disclosed herein for calibrations of all CT scanners for densities without the use of water phantoms. The method uses known properties of internal tissues, namely fat, muscle, blood, air and cortical bone to perform calibrations by computational means with only the computer software disclosed herein. The methods here disclosed can use the new methodology to calibrate CT scanners for routine clinical imaging with no requirement for scans of any external phantoms. The calibrations by the new method are more consistent for individual patients, are more accurate for quantitative measurements, are more standardized among different CT scanners, and are influenced less by variable scan techniques. The disclosed methods can provide full torso calibrations or calibrations based on a portion of the body, such as, for example, calibrations in the chest using in vivo air, and the ability to perform default calibrations in cases of extremes of fat, muscle, or air contents.

The methods enable the development of a new density scale for CT images, termed herein as the "Gram Scale" with new voxel intensity units, here termed Gram Units (GU). The GUs can be directly converted to physical densities and provide an image display scale subjectively equivalent to the HU scale. The resulting images can also be used to automatically set improved patient specific window/levels for viewing or recording without operator interaction.

The new calibration method greatly improves the reliability of MDCT images for quantitative imaging. The reported large differences between single slice and MDCT scanners can be conveniently corrected with the method disclosed herein. Scans of patients on older single slice scanners and repeat scans on MDCT can now be compared on the same density scale.

A new calibration reference point is disclosed herein. The new calibration reference point, termed the Soft Tissue Reference (STR), is uniquely defined as the 50/50 percentage point between the outer half-maxima of the intensity distribution (histogram) of voxel intensities of two known tissues. The STR is minimally affected by noise, tissue mixing, scan conditions and different scanners in contrast to known prior methods and is highly robust because the 50/50 point is reliably independent from these variables. The STR can be used for routine calibrations for any CT scanner while providing improved calibrations over standard water phantom methods. The STR can be computed for different combinations of tissue types, such as in-vivo air and fat, muscle and fat, cortical bone and muscle. The STR can alternatively be used to calibrate water equivalent HU scale based images as currently used in conventional methods and without using water phantoms. The STR can be used advantageously in dual-energy or multi-energy or so-called mono-energetic CT imaging where the robust STR calibration point or points can be carried through the several image processing steps. The disclosed methods can be applied to any 3-dimensional imaging system including tomosynthesis or 3-D DXA devices. The STR is computed automatically in background mode.

The STR can be stored for continuous monitoring of the CT scanner calibration and for reporting changes over time to the operator or the manufacture.

BRIEF DESCRIPTION OF THE DRAWINGS

Embodiments in accordance with aspects of the present invention are described below in connection with the attached drawings in which:

FIG. 11 illustrates the structure of the Gram Scale, including the tissue densities, expected HU values for these tissue densities and compared to the expected GU values for the tissue densities;

FIG. 12 illustrates a simplified comparison of the Gram and HU scales. The relative water density of 0 HU as the central calibration point for water based calibrations in the HU scale and the STR relative density of −26 mg/cm$^3$ as the central calibration point for the GU Scale are represented;

DETAILED DESCRIPTION OF PREFERRED EMBODIMENTS

A system and method for calibration of CT scanners and display of images in density units without the use of water phantoms is disclosed herein with respect to exemplary embodiments. The embodiments are disclosed for illustration of the system and methods and are not intended to be limiting except as defined in the appended claims.

Figure 1:
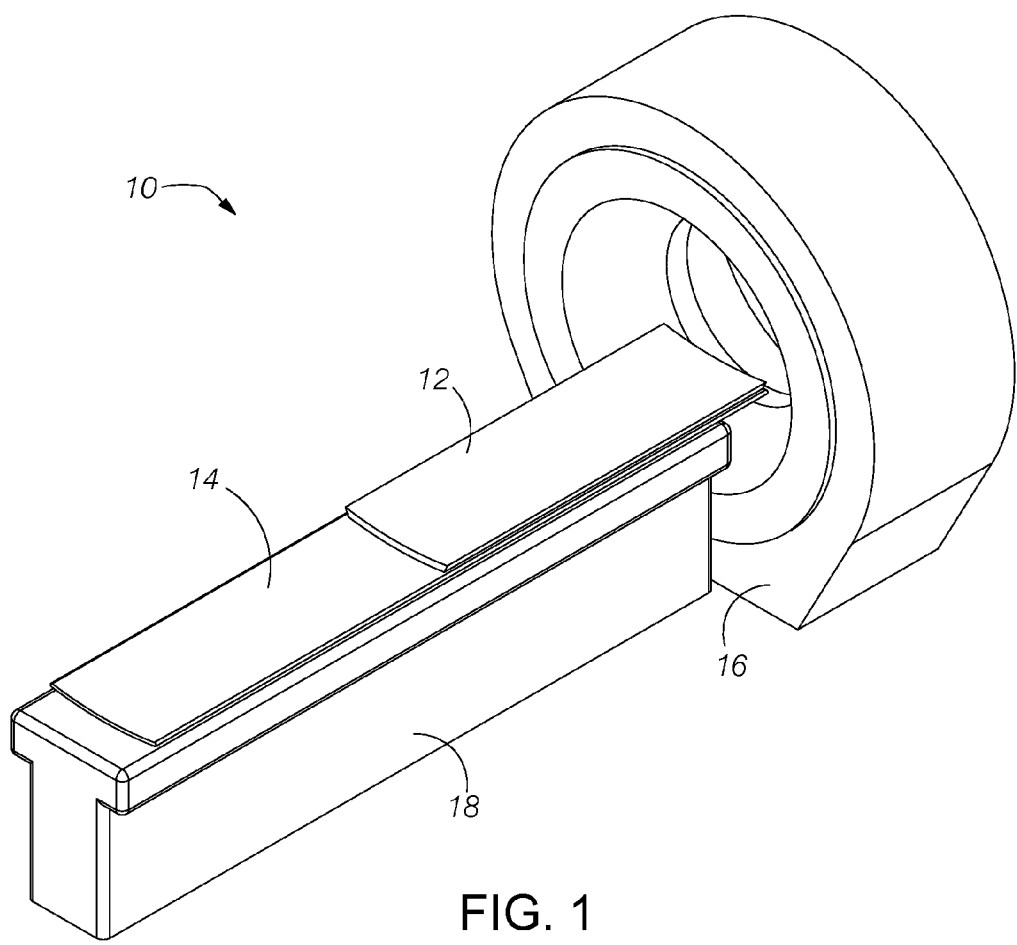
FIG. 1 illustrates a partial perspective view of an embodiment of a CT scanner with table and couch pad for patient support proximate to the gantry containing x-ray source and detectors.

A representative embodiment of an exemplary CT scanning system 10 is shown in FIG. 1. The system includes a CT scanner 12, which is represented pictorially as a large toroidal chamber. The system includes a cushion or patient support pad 14 positioned on a CT scanner table 16 proximate to the scanning portal of the CT scanner. The scanner table rests on a support platform 18. One skilled in the art will appreciate that during an imaging procedure, a subject is placed on the scanner table. The scanner table moves longitudinally with respect to the top of the support platform to move the support pad and the subject into the portal of the CT scanner to position a particular portion of the patient's body in the target area of the CT scanner to be imaged therein. The scanner table is also movable to allow multiple slices of images to be generated during the same procedure to provide the images needed to create a three-dimensional set of images of a selected volume within the patient's body.

Figure 2:
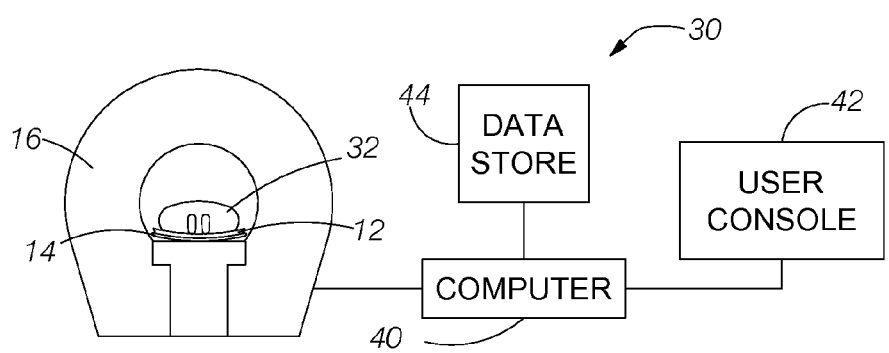
FIG. 2 illustrates an exemplary processing system for implementing the methods in accordance with the present invention.

FIG. 2 illustrates an exemplary system 30 that implements the method disclosed herein in combination with the CT scanning system 10 of FIG. 1. In particular, a patient 32 is shown positioned on the support pad 14 within the CT scanner 12. The measurements from the CT scanner are electronically communicated to a data processing subsystem (computer) 40 that operates in accordance with the software method described below. The computer is coupled to a user console 42 (comprising, for example, a display device, one or more data entry devices and a cursor control devices) and to a storage unit (data store) 44. The console and the storage unit may be part of the computer or may be external components. The measurements may be communicated directed from the CT scanner to the computer or may be stored and then later communicated to the computer. Although shown as a separate unit, the computer may be included as part of the CT scanner.

The CT scanner 12 of FIGS. 1 and 2 operates in a conventional manner to image a selected volume of the body of the patient 32 to create digitized images comprising voxels having intensity levels that represent the attenuation of the x-ray beams that penetrate the body during the imaging procedure. In particular, the CT scanner produces a plurality of CT images that are stored in the data store 44. The method described below processes the plurality of images to provide calibrated information regarding the attenuation of the x-ray beams so that images generated by different scanners or by the same scanner under differing conditions can be compared to accurately determine changes in the patient's condition.

The disclosed methods start with a CT scan of most any portion of the body. The scan could have been made for a variety of diagnostic purposes and with a variety of scan parameters or scanners. No phantoms need to be scanned with the patient or independent from the patient including water phantoms. The scan may or may not include bone in the displayed field-of-view, but will likely include bone. The disclosed methods automatically set a measurement volume-of-interest (VOI) within the images as best understood with reference to the flow charts in FIG. 3 and FIG. 4.

Figure 3:
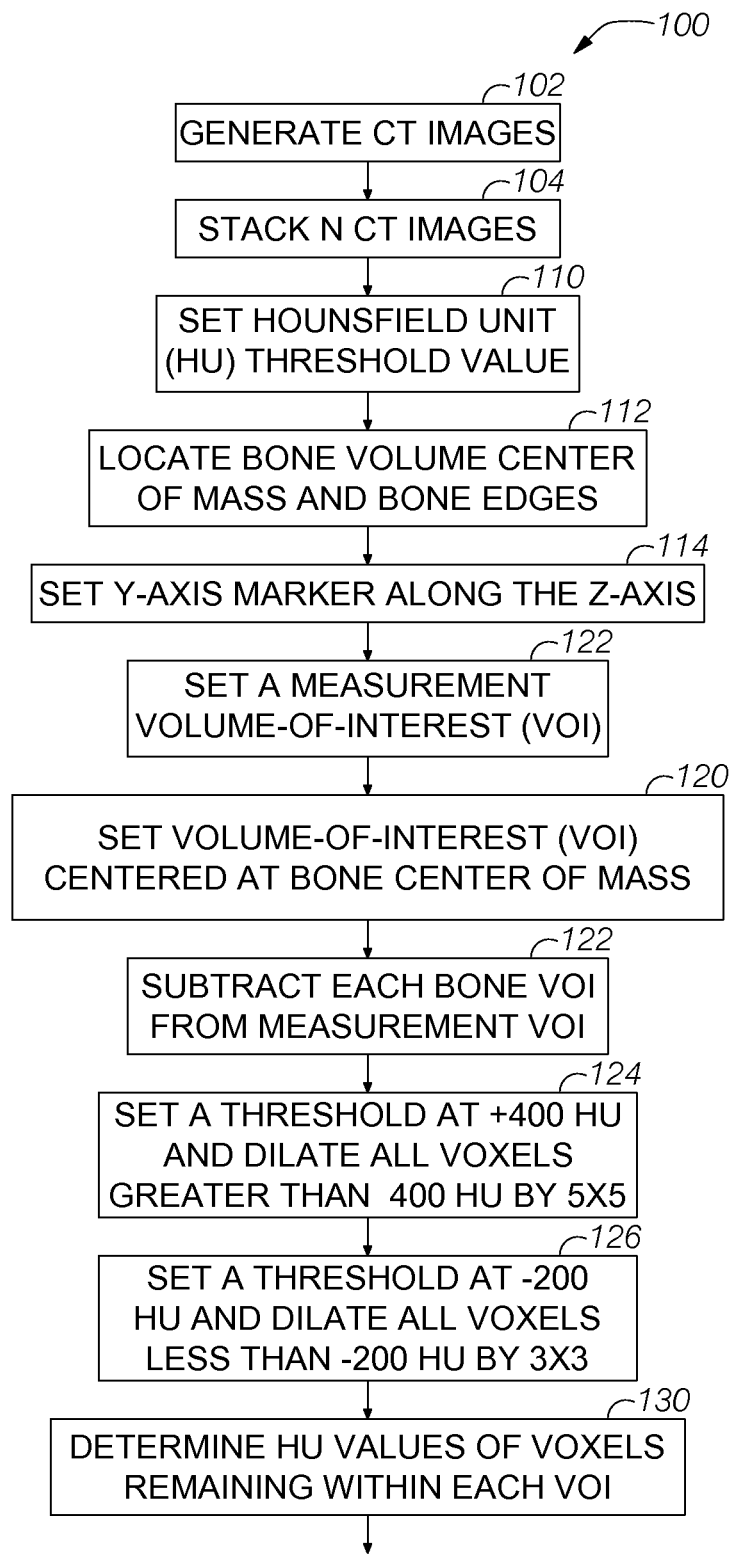
FIG. 3 illustrates a flow chart of the steps of software computations to automatically position a measurement volume-of-interest (VOI) for extracting voxel intensities and for exclusion of unwanted voxels for background subtraction in accordance with embodiments of the invention.

FIG. 3 illustrates a flow chart 100 of the method in accordance to an illustrated embodiment. The method first forms a plurality of CT images in a step 102 using the CT scanner 12 of FIGS. 1 and 2, for example. The method stacks N of the CT images in a step 104. The number N may have a preset value, or the number N may be a variable parameter that may be changed in accordance with the thickness of the slices generated during a particular scan.

In a step 110, the method sets a Hounsfield Unit (HU) threshold value for bone, typically on the order of +400 HU. The bone threshold exact value is not critical but necessary to automatically identify likely bone voxels.

In a step 112, the method computes the bone volume center-of-mass (CoM) by standard methods known in the art. The method also locates the edges of the bone volumes. These anatomical targets are used for automatic positioning the measurement volume VOI. Other anatomical targets may also be used such as the exterior margins of the body or air spaces in the body. These markers mush be unambiguous and reproducible.

After locating the bone volume CoM and the bone edges in the step 112, the method sets a y-axis marker along the z-axis located at the anterior edge of and including the bone volumes and extending to the posterior margins of the patient body to define the measurement VOI in a step 114. In a step 116, the method uses the y-axis marker generated in the step 114 to set the VOI that includes a significant portion of the subject's body. Preferably, each VOI is positioned to avoid the liver (e.g., the VOI is positioned at the posterior of the patient's body or on the right side of the body. If another object is present below the patient such as a phantom for Hybrid calibrations or the tabletop, these are removed by segmentations. The VOI may alternatively be positioned at some fixed distance from these anatomical markers or edges. Further the VOI may be further divided into smaller VOIs and of different geometries. For example, the original VOI may be elliptical in shape and fit to the exterior cross-sectional margins of the patient. A plurality of VOIs may be determined. For example, the VOI may be divided into increasingly smaller rings allowing measurements more central and more peripheral in cases of special differences in voxel intensities. The size of the VOI is determined based on scanner slice thickness and the noise of the images. The method can further extract DICOM headers of the images to incorporate other scan parameters for improved estimation of preferred VOI size.

In a step 120, the method sets a circular bone VOI centered at the bone center-of-mass. The circular VOI is computed to be larger than the bone volume. Then, in a step 122, the bone VOIs are subtracted from the original measurement VOI and not included in further calculations.

Figure 5A:
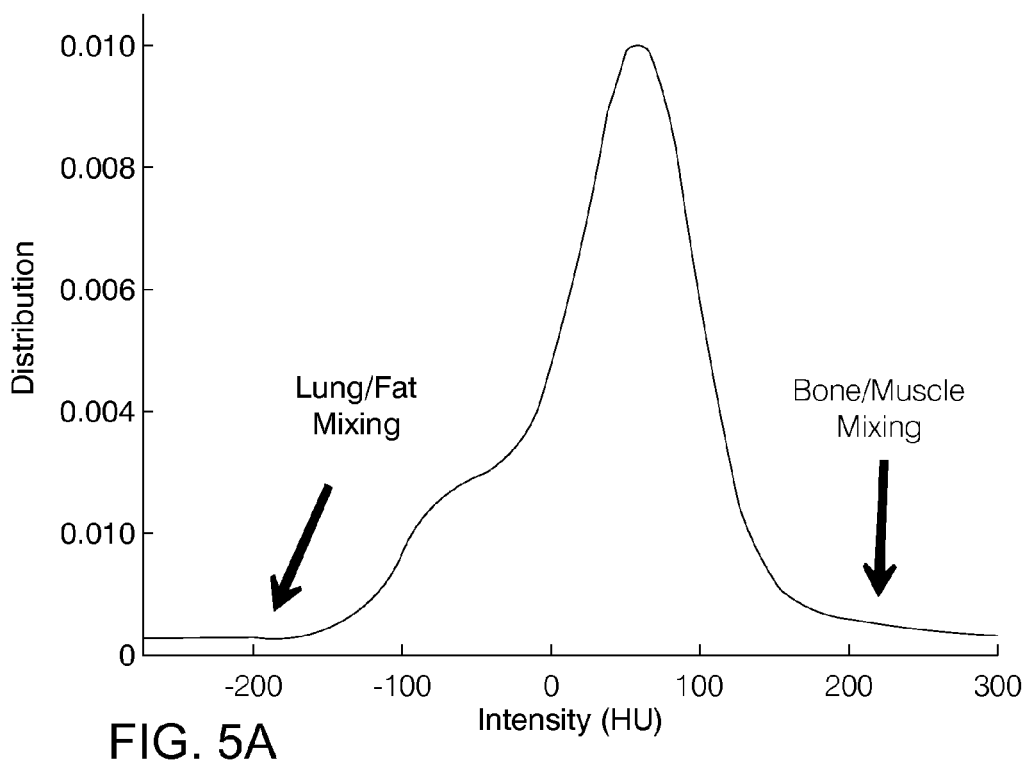
FIGS. 5A and 5B illustrate computed voxel intensity distributions (un-normalized histograms) of a subject before (FIG. 5A) and after (FIG. 5B) background subtraction as disclosed in FIGS. 4A and 4B.
Figure 5B:
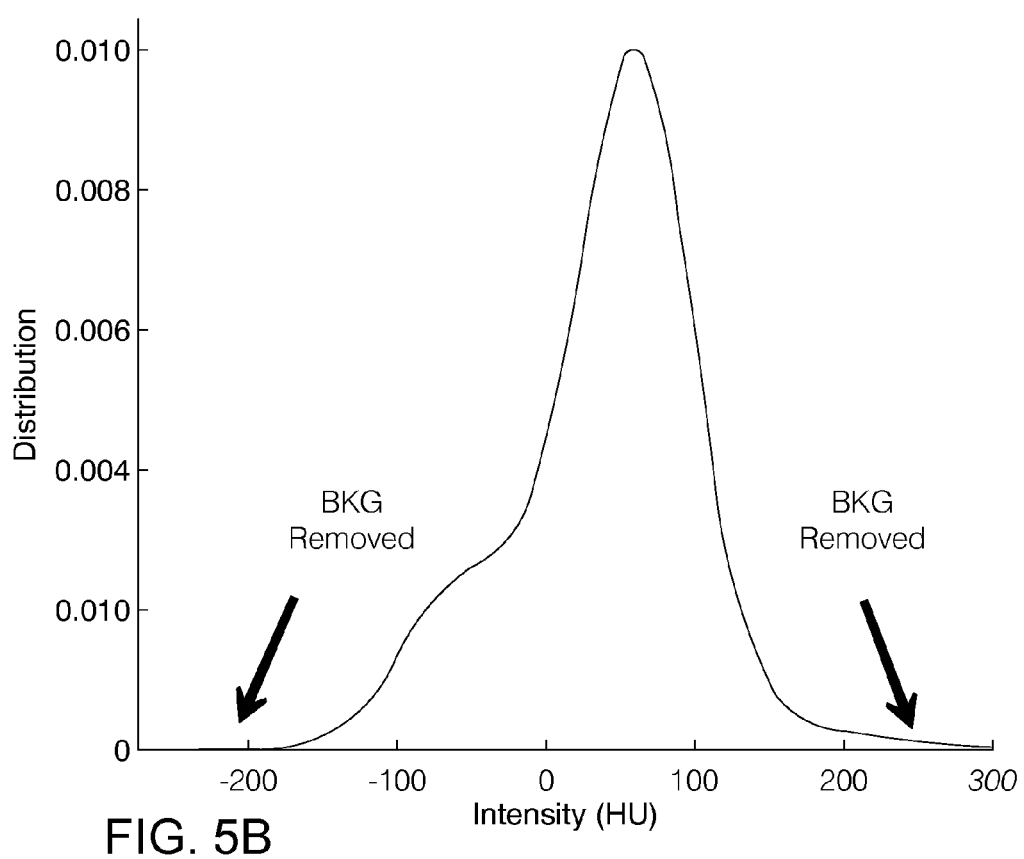

In a step 124, the method using the bone threshold of +400 HU performs a 3-D dilation of all voxels within the VOI greater than +400 HU by 5 voxels. The method then sets a threshold at −200 HU and dilates all voxels less than −200 HU by 3 voxels in a step 126. These two dilation steps further reduce the VOI used in further calculations. The combined steps described in 124 plus 120 provide a kind of background (bkg) subtraction of unwanted voxels. FIGS. 5A and 5B illustrate an example intensity distribution before (FIG. 5A) and after (FIG. 5B) background subtraction.

A major barrier to the execution of the disclosed methods was to distinguish voxels containing partial volume mixtures of bone and fat or air and fat that produced voxel intensities indistinguishable from fat or muscle voxels, for example. The trabecular bone within the vertebral bodies of the spine is such an example where trabecular bone and vertebral fat and/or blood are frequently contained within many of the voxels and produce partial volume intensities in the muscle range. In a similar fashion, air within the chest or lung tissue is mixed with soft tissue particularly at the edges of air/lung and the interface with soft tissue and/or calcifications. The methods disclosed above were found to successfully remove these unwanted voxels from the calibration measurement volumes.

In a step 130, the method determines the intensity values of all voxels remaining within each VOI (e.g., the voxels that were not removed by the dilation in steps 124 and 126 the bone removal step 122.

Figure 4A:
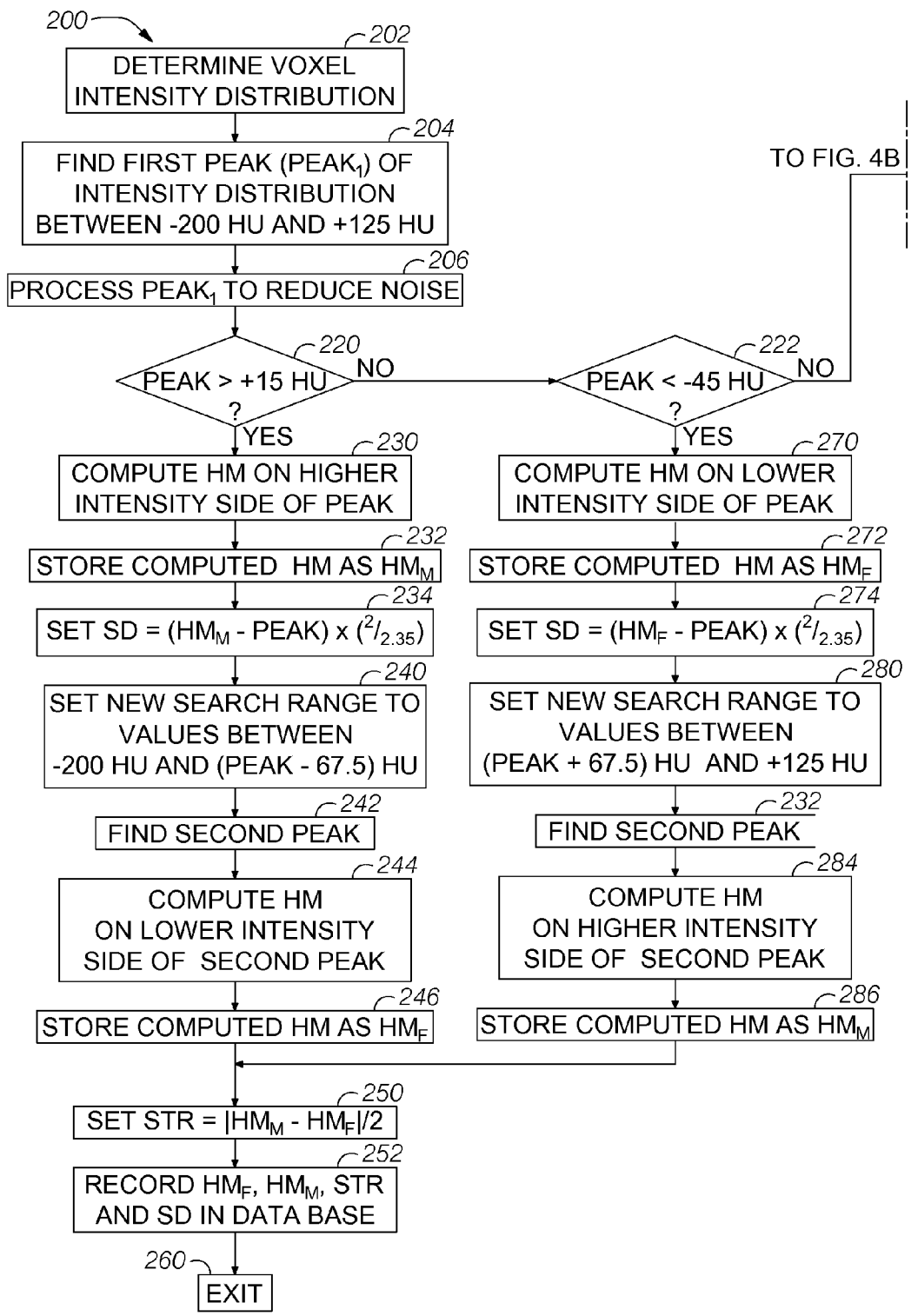
FIGS. 4A and 4B illustrate a flow chart of the calibration computations of the STR using the voxel intensities of the tissues defined and extracted by the method of FIG. 3.
Figure 4B:
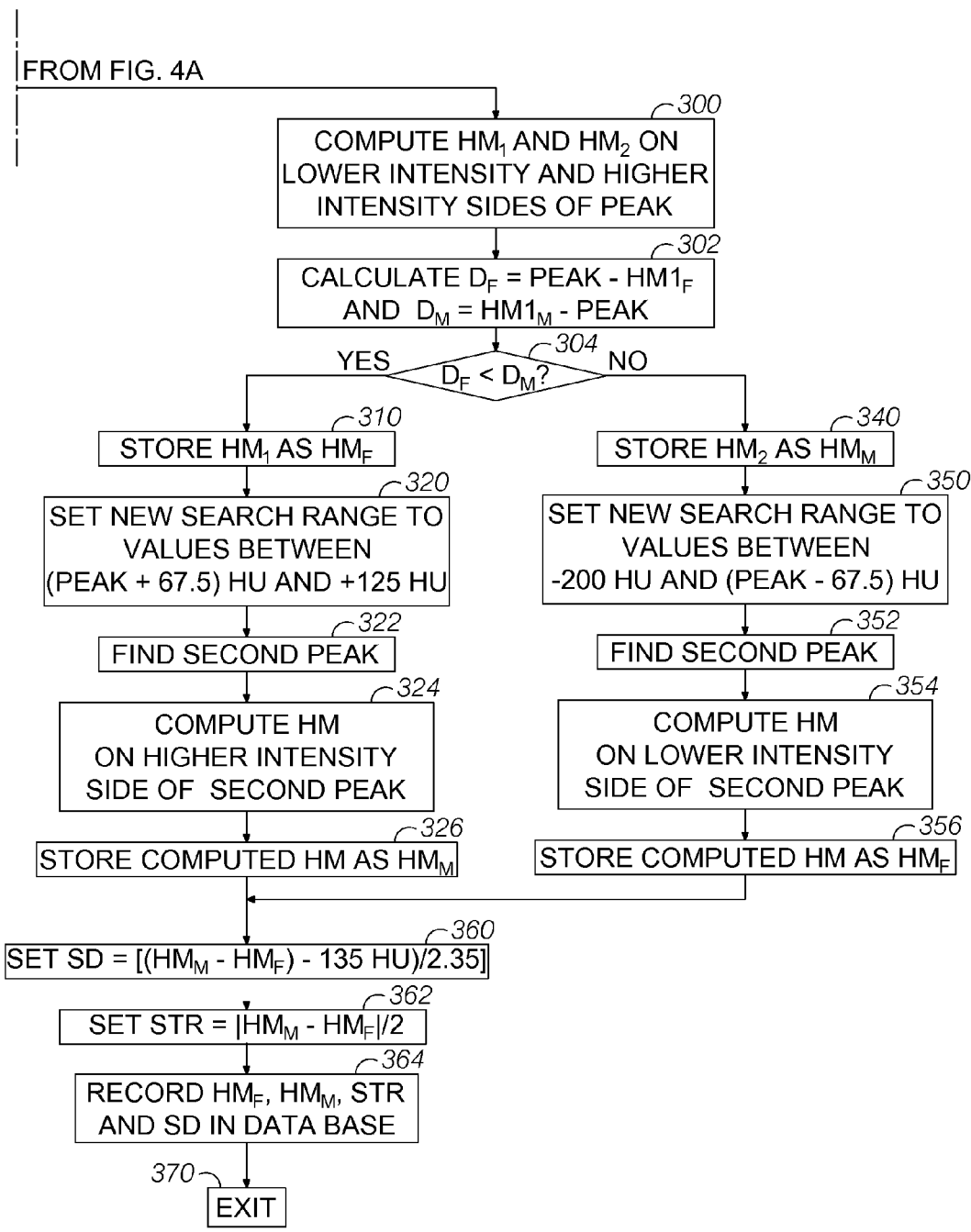

The method further processes the images in accordance with a flow chart 150 illustrated in FIGS. 4A and 4B. The flow chart in FIGS. 4A and 4B illustrate the STR calibration computation using the voxel intensities of the tissues defined and extracted by the method illustrated in the flow chart 100 of FIG. 3.

In a step 202 (FIG. 4A), the method determines the intensity distribution of the voxels remaining in the step 130 of FIG. 3. The distribution comprises the number of voxels at each intensity value versus the voxel intensity value. The intensity values may be HU or other units reconstructed by the scanner.

In a step 204, the method finds the first peak of the measured intensity distribution ($Peak_1$) within the preferable range between −200 HU and +125 HU. $Peak_1$ may represent voxels mostly corresponding to fat or voxels corresponding to muscle or may represent a blended peak of fat and muscle with only one discernible peak.

In a step 206, the method processes the first peak ($Peak_1$) to reduce noise. In particular, within the step 206, the method establishes a range of values within 5% of this peak ($Peak_1$) found in the step 204. The method then calculates an average intensity value of the pixel values within this range. This step essentially computes a new peak that is not the mode or the mean of the distribution but rather a mean of voxel intensities around the initial peak. This step was found to remove noise and small fluctuations in the peak value. This calculated average intensity value then replaces the initial distribution $Peak_1$, which is identified herein as PEAK.

In a first branching decision step 220, the method determines whether PEAK is greater than +15 HU. If PEAK is not less than +15 HU, the method proceeds to a second branching decision step 222, wherein the method determines whether PEAK is less than −45 HU. If PEAK is not less than −45 HU, the PEAK must necessarily be between −45 HU and +15 HU. If PEAK is between −45 HU and +15 HU, the method branches to a set of steps, which are described below in connection with FIG. 4B.

Figure 6:
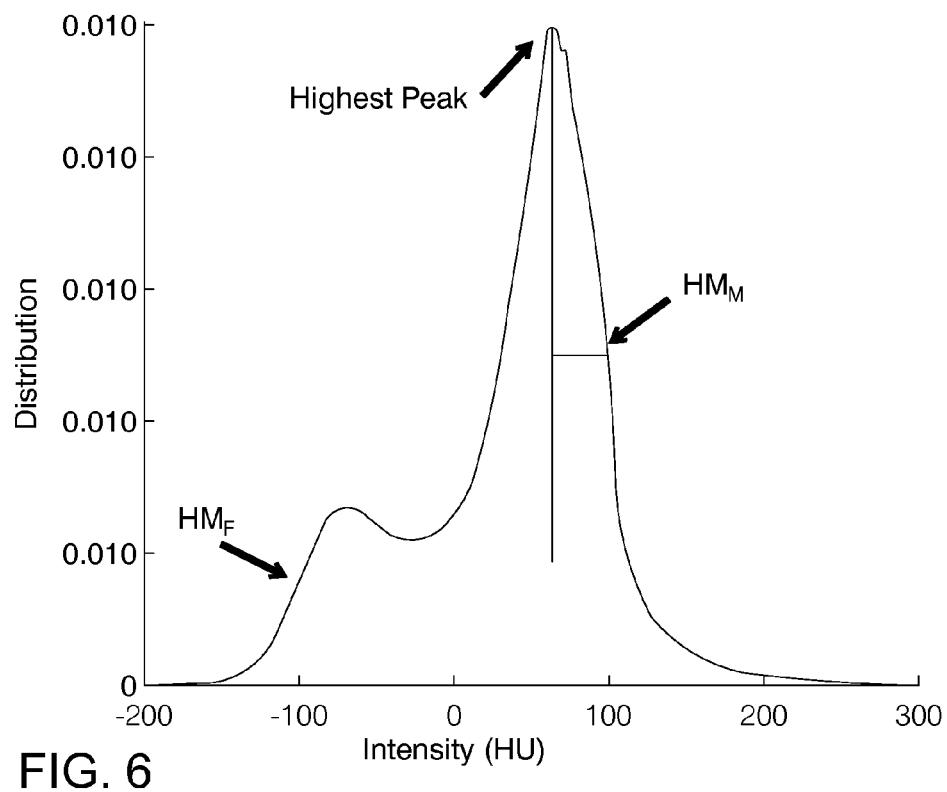
FIG. 6 illustrates an example of voxel intensity distribution of a subject with a muscle dominant first peak, which shows the dominant side half maximum ($HM_M$) of the peak and the right (dominant) side portion of the full-width-at-half maximum (FWHM) of the peak.

If PEAK is greater than +15 HU in the first branching decision step step 220, PEAK is taken as a muscle dominant peak. FIG. 6 shows a representative muscle dominant intensity distribution. It can be seen that the right peak, muscle, is a higher peak and will be detected first by the disclosed algorithm described in FIG. 4A. The method branches from the decision step 220 to a step 230, wherein the method computes the half-maximum intensity value of the first peak on the higher intensity (right) side of the muscle peak. This side contains much less mixing of fat and muscle approaching no mixing. The computed value is identified as $HM_M$ and is stored in a step 232 to indicate that the value is a half maximum value corresponding to muscle tissue. In a step 234, the method calculates an estimate of the peak standard deviation (SD). FIG. 6 shows representative marks at the peak value and the HM value, thus depicting the SD value as the difference in the two values. The higher intensity side of the peak is noted to be Gaussian and contains much less tissue mixing than the lower intensity side that has a broader spread. It is recognized by those skilled in the arts that the SD of a Gaussian distribution can be computed by $$SD=(HM_M-PEAK)\times(2/2.35).$$

In the step 240, the method sets a new search range between −200 HU and a new upper limit calculated as (PEAK−67.5 HU). It should be understood that this has the effect of removing the muscle peak from the new search range. Limited within the new search range, the method finds a second peak ($PEAK_2$) in a step 242, which corresponds similarly to the sequence of steps 204-206, described above. This peak, if existing, is likely represented by fat voxels and is located in an expected lower intensity range. The subtraction or addition of 67.5 HU was determined to reliably exclude one peak and uncover the second peak in most subjects. Then in a step 244, the method computes the half-maximum (HM) of the second peak on the lower intensity side of $PEAK_2$. The method stores this computed HM value of the second peak as the half-maximum value for fat identified as $HM_F$ in a step 246.

In a step 250, the method computes the soft tissue reference point (STR) based on the original half-maximum value for muscle ($HM_M$) and the second calculated half-maximum value of the uncovered fat peak ($HM_F$). In particular, the STR is calculated by one-half of the absolute difference between $HM_M$ and $HM_F$ (e.g., $STR=|HM_M-HM_F|/2$). Then, in a step 252, the $HM_F$ and $HM_M$ values are recorded in a database (e.g., within the data store 44 of FIG. 2) along with the calculated STR value and the calculated SD value. The method then exits via a common exit step 260.

Figure 7:
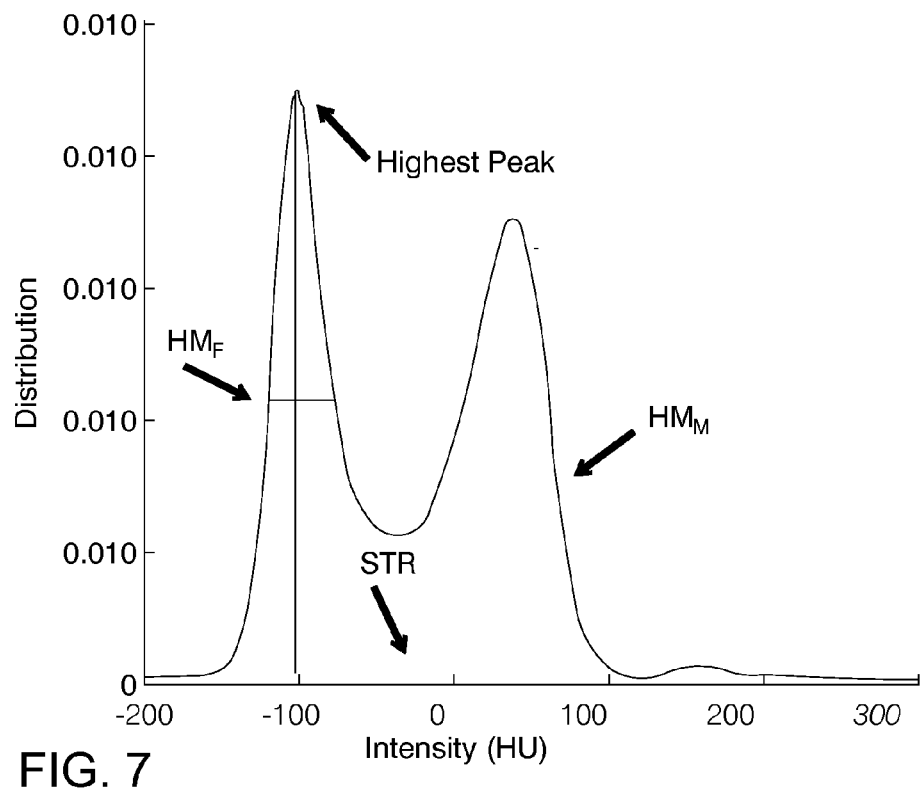
FIG. 7 illustrates an example of voxel intensity distribution of another subject with a fat dominate first peak, wherein the peak and left (dominant) side half of the FWHM are shown.

If PEAK is less than −45 HU in the second branching decision step 222, then in a step 270, the method computes the half-maximum intensity value of the first peak determined on the low intensity (left) side of PEAK. The computed value is identified as $HM_F$ and stored in a step 272 to indicate that the value is a half maximum value corresponding to fat tissue. FIG. 7 shows a representative distribution with a fat dominant intensity distribution. The fat peak is larger than the muscle peak and is so identified first by the methods of FIGS. 4A and 4B. In a step 274, the method then calculates the SD of the example fat dominate peak as $SD=(PEAK-HM_F)\times(2/2.35)$. A fundamental assumption of this method is that the SDs of muscle dominated and fat dominated peaks are substantially equal. This assumption has been tested on many subject scans with confirming results. The method then proceeds to a step 280.

In the step 280, the method sets a new search range between a new lower limit calculated as (PEAK+67.5) and the original upper limit of +125 HU. It should be understood that this has the effect of excluding the fat peak and uncovering the second peak in the upper intensity range. Using the new search range, the method finds a second peak ($PEAK_2$) in a step 282, which corresponds to the sequence of steps 202-206, described above. Then in a step 284, the method computes the half-maximum (HM) of the second peak on the higher intensity side of $PEAK_2$. The method stores the second HM value as the half-maximum value for muscle identified as $HM_M$ in a step 286.

After storing the $HM_M$ value in the step 286, the method proceeds to the step 250, which is common to the determination of $HM_M$ and $HM_F$ when the originally determined PEAK is either greater than +15 HU at the decision step 220 or is less than −45 HU at the decision step 222. Accordingly, in the step 250, the method computes a soft tissue reference point (STR) based on the original half-maximum value for fat ($HM_F$) and the second determined half-maximum value for muscle ($HM_M$). In particular, the STR is calculated by one-half of the absolute difference between $HM_F$ and $HM_M$ (e.g., $STR=|HM_F-HM_M|/2$). Then, in the step 252, the $HM_M$ and $HM_F$ values are recorded in a database (e.g., within the data store 44 of FIG. 2) along with the calculated STR value and the calculated SD value. The method then exits via the common exit step 260.

Figure 8:
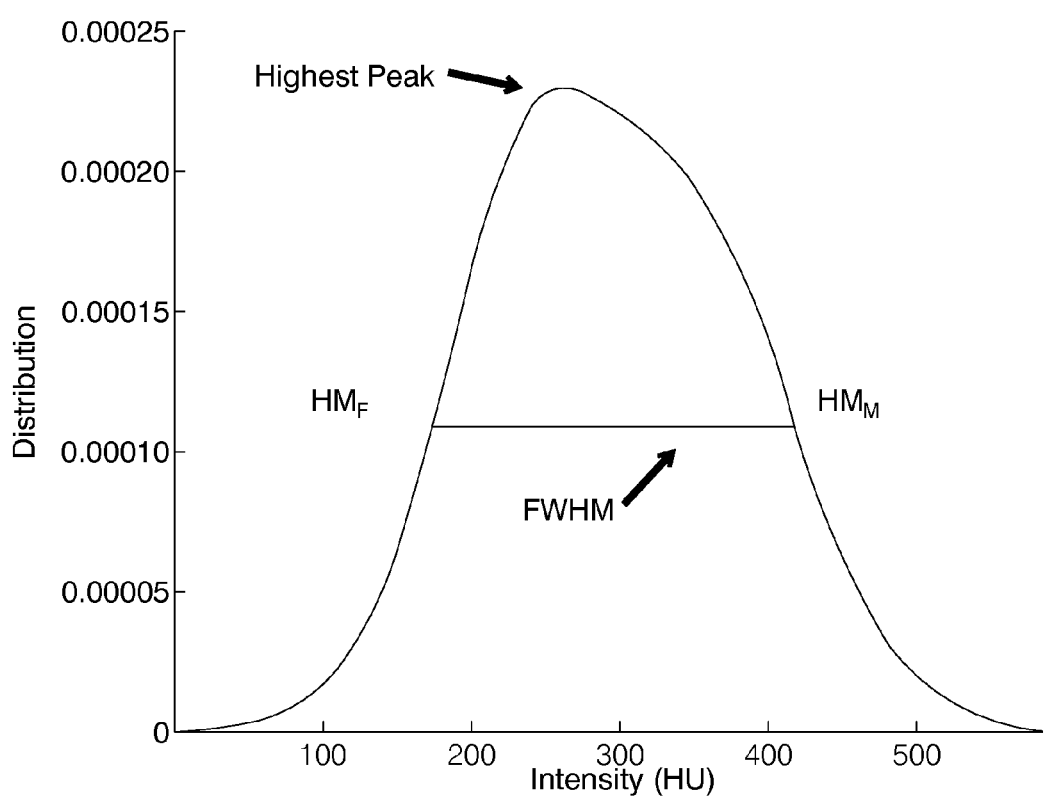
FIG. 8 illustrates an example of voxel intensity distribution of a third subject with only one peak with a broad distribution (identified herein as a "blended peak")

If the original PEAK is between −45 HU and +15 HU, as determined by the NO branches from the first branching decision step 220 and from the second branching decision step 222, the distribution is deemed to be a blended peak and the method proceeds to a step 300 shown on FIG. 4B. FIG. 8 shows an example of a blended peak. The intensity distribution is broad where both fat and muscle are included and the images may include high noise. Also, only one discernible peak is present. As discussed above with respect to the steps 202-206 in FIG. 4A, the top 5% of the found first $Peak_1$ is averaged to smooth and improve the estimate of the final peak. This corrected new peak is recorded as PEAK. In the step 300 of FIG. 4B, the method computes a value $HM_1$ as the half-maximum of the PEAK on the high intensity side and also computes the half-maximum value $HM_2$ of the PEAK on the low intensity side. Note that these two HM values essentially define the FWHM of the total blended peak. Then, in a step 302, the method calculates the differences $D_M$ or $D_F$ between the PEAK and the two HM values: ($D_M$=(PEAK−$HM_1$)) and $D_F$=($HM_2$−PEAK)). Then, in a decision step 304, the method determines whether $D_F$ is less than $D_M$ in order to determine which way the 67.5 jump in the search range will be applied.

If $D_F$ is less than $D_M$ ($D_F<D_M$ is true) in the decision step 304, $HM_1$ is set as the half-maximum value $HM_F$ for the fat side in a step 310. The lower limit of the search range is increased to PEAK+67.5 in a step 320, and a second peak is identified in a step 322, as described above. The HM of the second peak is determined on the higher intensity side in a step 324. The HM is identified as $HM_M$ and stored in the database in a step 326.

If $D_M$ is less than $D_F$ ($D_M<D_F$ is true) in the decision step 304, $HM_2$ is set as the half-maximum value $HM_M$ for muscle in a step 340. The upper limit of the search range is reduced to PEAK−67.5 in step 350, and a second peak is identified in a step 352, as described above. The HM of the second peak is determined on the lower intensity side in a step 354. The HM is identified as $HM_F$ and stored in the database in a step 356.

After completing either the step 326 or the step 356 in accordance with the branch taken at the decision step 304, the method proceeds to a step 360. In the step 360, the method calculates an SD value from the final HM values established in the selected branch. Here in the case of a blended peak, the SD is computed by SD=(|$HM_M$−$HM_F$|−135 HU)/2.35.

In a step 262, the method computes the STR in accordance with the prior steps. The method then stores $HM_M$, $HM_F$, SD and STR in a step 264 before exiting via an exit step 270.

It will be apparent to one skilled in the art, that the above disclosed methods can be applied to other measures of tissues in addition to HMs, such as averages, modes, etc., while using the above disclosed steps.

Figure 9:
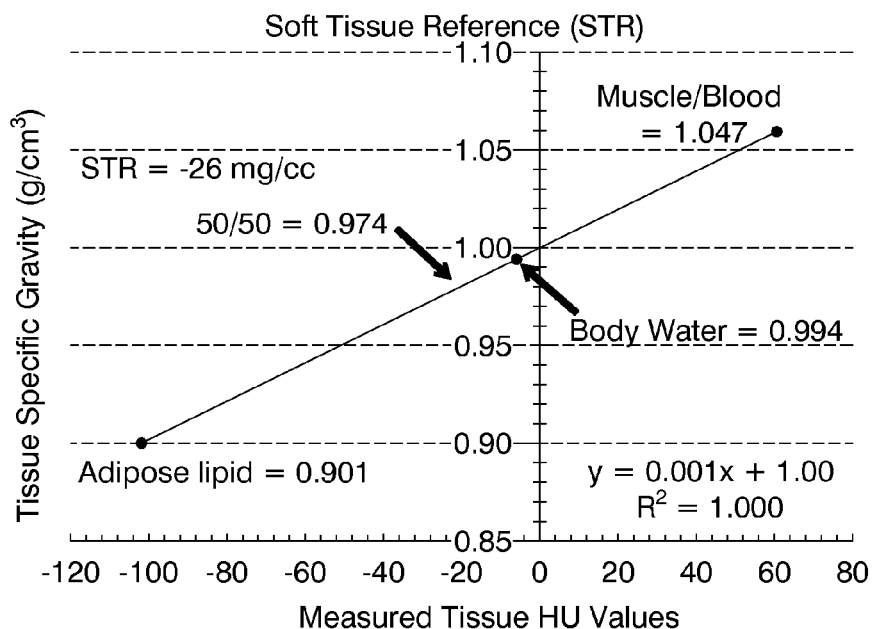
FIG. 9 illustrates a graph demonstrating how the 'Soft Tissue Reference' (STR) is computed from the two measured half maxima ($HM_F$ and $HM_M$) of two tissues, wherein the y-axis shows the known densities of the two tissues and the computed density of the 50/50 voxel, and wherein the x-axis shows the measured voxel intensities of the $HM_M$, $HM_F$ and 50/50 voxel intensity, and wherein the computed density of water at body temperature is also shown.

FIG. 9 illustrates the computation of the STR calibration factor using the measurement results and computed measured STR in intensity units or HU units demonstrated in the flow charts shown in FIG. 3 and FIGS. 4A and 4B. Using the known densities of fat 0.9001 g/cm$^3$ and muscle 1.047 g/cm$^3$, determine that voxels with 50% muscle and 50% fat will have a known density of 0.974 g/cm$^3$. (Note that other published specific gravities of tissues or experimentally measured tissue densities may be used). The known reference density of water (1.000 g/cm$^3$) with HU value of 0 is also shown. The expected density of water at body temperatures, body water, is noted to be well defined on the regression line. These known reference values are shown on the y-axis of FIG. 9. The computed density of the known STR can be expressed in mg and referenced to water by STR=[974 mg/cm$^3$−1000 mg/cm$^3$] or −26 mg/cm$^3$.

The known STR will thus have a delta in density from water of −26 mg/cm$^3$ that can be used to calibrated CT scanners by these methods back to water based HU values. With conventional water calibration the intensity value for a water phantom is measured in HU units and the HU scale is calibrated to water equal to 0. With the newly disclosed methods, the STR measured intensity is determined by the detailed steps of FIGS. 3 and 4. The scanner is then calibrated to −26 mg/cm$^3$ for the STR in the Gram Scale. Conversion of the then calibrated CT scanner in GU units can be converted to calibrated HU units by simply shifting the voxel intensities by −26 mg/cm$^3$ and defining this as the new HU value (0) of water. This so determined −26 mg/cm$^3$ value for muscle-fat calibration is defined herein as the "Soft Tissue Reference (STR) known" density in the Gram Scale.

Figure 10:
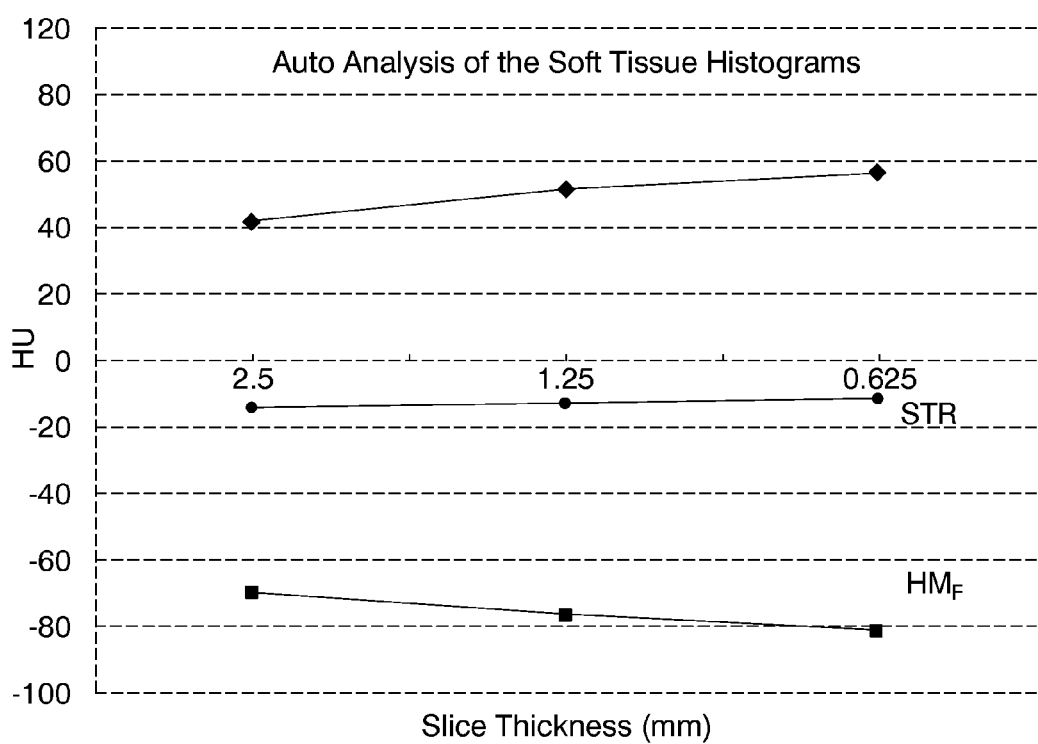
FIG. 10 illustrates measurements and computations of the $HM_M$ and $HM_F$ and STR determined from one patient CT scan reconstructed at three slice thickness.

FIG. 10 show example measurements and computations of the $HM_M$ and $HM_F$ and STR determined from one patient CT scan reconstructed at three slice thickness. The noise is seen to increase with thinner slices resulting in larger full-width-at-half maxima (FWHM) of the peaks, wherein the HMs are seen to vary in direct relationship with the SD computed from the half value of the FWHM, and wherein the computed STR is shown to be immune to these variables demonstrating a robust calibration point.

FIG. 11 shows the construct of the Gram Scale. The known densities of fat 0.9001 g/cm$^3$ and muscle 1.047 g/cm$^3$, and the 50% muscle and 50% fat voxel known density of 0.974 g/cm$^3$ are shown. The reference density of water (1.000 g/cm$^3$) with HU value of 0 is also shown. The computed density of the known STR of −26 mg/cm$^3$ is seen to take a comparable central reference role as water as the universal standard in GU. The known STR has the delta in density from water of −26 mg/cm$^3$. FIG. 11 demonstrates that the Gram Scale reflects similar ranges of intensity units to the HU scale.

There may be advantages to changing the ranges, as has been done with the HU scale over the years, and such changes would not distract from the GU scale's usefulness or the underlying methods. For example, it may be advantages to extend the bone range to a higher range.

FIG. 12 illustrates a more simplified comparison of the Gram and HU scales using the relative water density of 0 HU as the central calibration point for water based calibrations in the HU scale and the STR relative density of −26 mg/cm$^3$ as the central calibration point for the GU Scale. It can be seen by those familiar with CT imaging that the scales are comparable and that displayed images in each will appear undistinguishable for general diagnostic work.

Apply the STF calibration Factor to the original and/or total images by multiplying the CT scanner recorded HU values of each pixel by the calibration factor to obtain images expressed in density units. From the CT scanner measured machine/patient HU value of the "STR" calibration point in CT numbers, calculate the Calibration Factor, CF=−26 mg/cm$^3$/STR (HU). Alternatively, set a prior HU for the STR density, preferably reference to water for continuity, and apply a shift of pixel HU value to achieve the water reference values.

Figure 13:
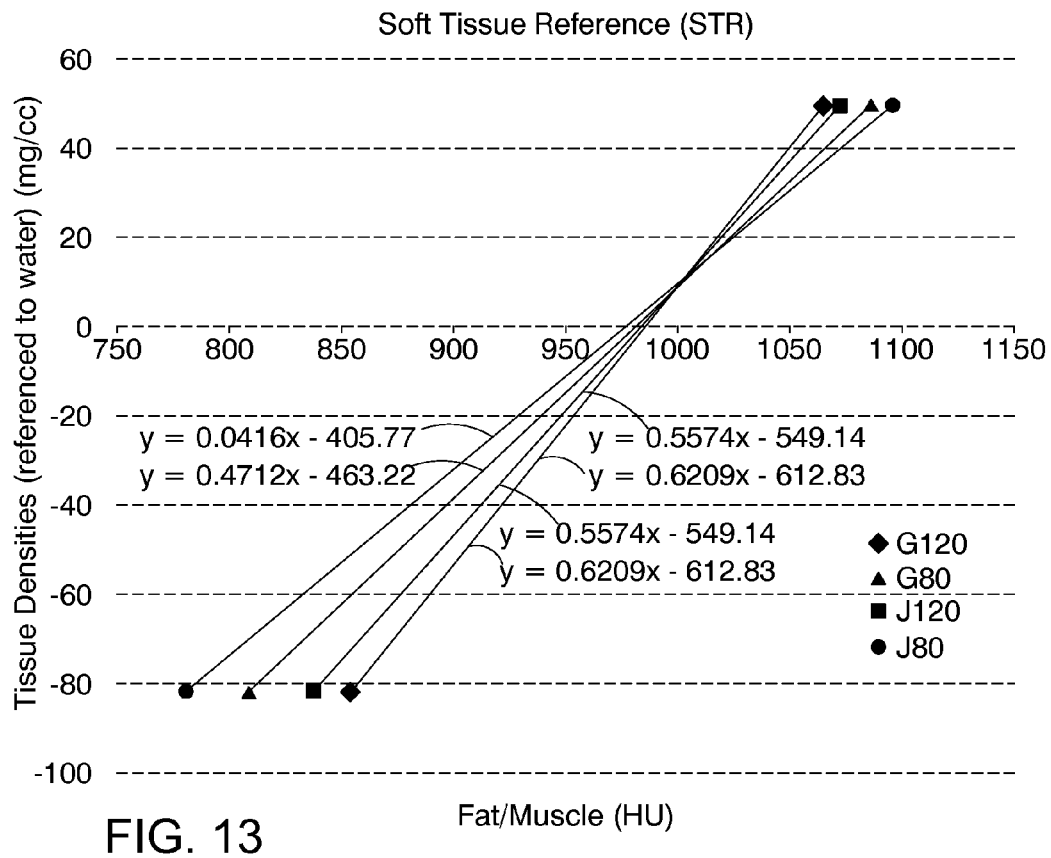
FIG. 13 illustrates measured and computed STR calibration data for two subjects scanned at two different beam energies on the same scanner.

FIG. 13 illustrates measured and computed STR calibration data for two subjects scanned at two different beam energies on the same scanner. The y-axis shows the known tissue densities expressed relative to water with a referenced density of 0, and wherein the x-axis shows the measured HU values of the half maxima (HMs) of the two tissue peaks determined for the two subjects and two kVps. The calibration regression lines all cross at approximately equivalent points suggesting the water calibration of this CT scanner by conventional means may be off by a few HU. The calibration lines also indicate that the HU values at the STR density are different at the two kVps indicating the x-ray energy dependence of even soft tissue and are also different for the two subjects indicating that conventional water calibration is not specific for individual patients.

Figure 14:
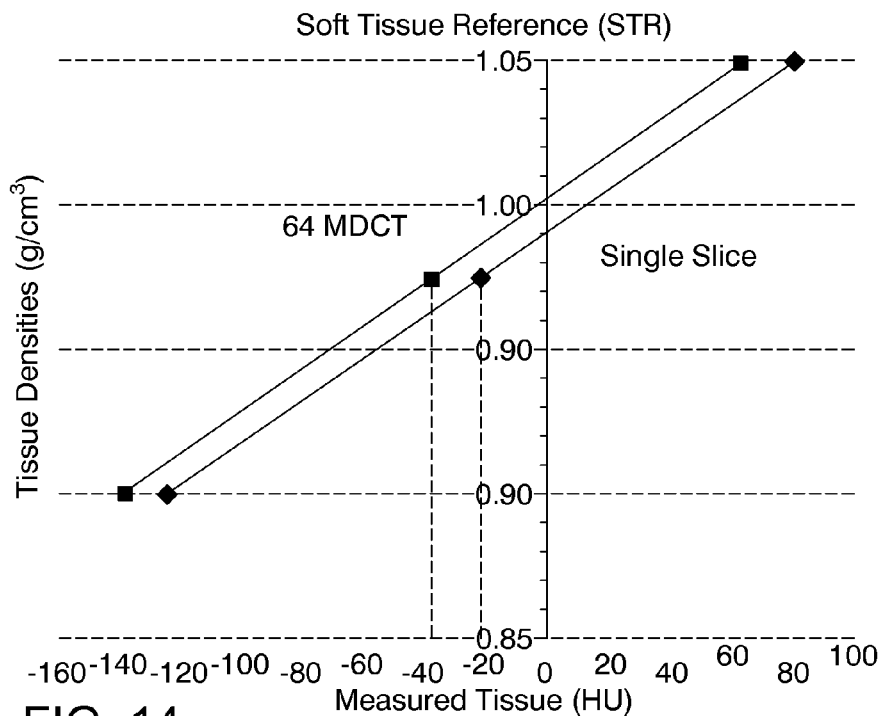
FIG. 14 illustrates calibration graphs of one subject scanned on two CT scanners using one embodiment of the disclosed methods.

FIG. 14 illustrates calibration graphs of one subject scanned on two CT scanners using one embodiment of the disclosed methods. The 64-slice MDCT scanner (because of the high scatter conditions and the manufacturer corrections for scatter) produced higher HU values than the single slice scanner on the order of +25 HU. The same patient was scanned on the same day and would be expected to produce the same measured tissue densities. The disclosed methods are shown to provide calibration and correction for these kinds of errors.

Similar STR calibrations can be made using other tissues or in-vivo materials. Lung density measurements are well known to vary widely under differing imaging conditions and such studies remain a problem. STR calibrations in chest CT can be accomplished by determining a different known STR for different tissues. For example, using the known density of air 0.0012 g/cm$^3$ (from $-10°$ C. to $+50°$ C., variability is about 0.2%) and fat. Since air, water, and soft tissues are relatively close in atomic composition, their HU values are determined by their relative densities to a very good approximation. Therefore, for example air at $-1000$ HU/0.0012 g/cm$^3$ or about 1 HU per 1.2 mg/cm$^3$ is comparable to the HU per mg/cm$^3$ difference between fat and muscle.

Since air in HU units is typically set to $-1000$ HU, an approximate mg/cm$^3$ value for a Soft Tissue Reference $STR_A$ for air and fat can be determined using in-vivo air measured in the chest or abdomen. The known densities then become 0.0012 g/cm$^3$ and 0.901 g/cm$^3$ for air and fat respectively. The known density of the 50/50 air/fat voxels is then computed to be 0.451 g/cm$^3$. The known $STR_A$ in the Gram Scale is then $-549.1$ mg/cm$^3$. The measured machine STR in HU units is computed in the same way as outlined in the flow charts 100, 200 and 300 described above.

As various changes could be made in the above constructions without departing from the scope of the invention, it is intended that all the matter contained in the above description or shown in the accompanying drawings shall be interpreted as illustrative and not in a limiting sense.

What is claimed is:

1. A method to calibrate computerized tomography scanners (CT) to produce image voxels expressed in Hounsfield Units referenced to water without the use of a water phantom by using only voxel intensities of tissues of a patient being scanned, the method comprising:
   determining at least one volumetric region of a CT scan that is positioned using computed anatomical measures;
   selecting unwanted sub-regions of the at least one volumetric region that are to be excluded from further analysis;
   determining the voxel intensity distribution of the at least one volumetric region after exclusion of the unwanted sub-regions;
   finding a first peak within the voxel intensity distribution;
   determining if the first peak is likely representative of a first identified tissue type having a first known tissue density;
   selecting a portion of the intensity distribution that does not include the first peak and finding a second peak;
   determining if the second peak is likely representative of a second identified tissue type having a second known tissue density;
   finding two voxel intensity measures representative of the two peaks of the voxel intensity distribution;
   finding a calculated voxel intensity half way between the representative voxel intensity measures of the two peaks and defining the calculated voxel intensity as a measured calibration reference point;
   computing a computed theoretical density of the calibration reference point using the known densities of the two identified tissue types; and
   using the measured calibration reference point and the computed theoretical density of the calibration reference point to compute calibrated voxel intensities in HU values.

2. The method of claim 1, wherein the sub-regions include bone, lung or air and voxels located within a distance equivalent to n pixels of the edges of the bone, lung or air.

3. The method of claim 1, wherein the two tissue types are muscle and fat.

4. The method of claim 1, wherein the two tissue types are in vivo air and fat.

5. The method of claim 1, wherein the two tissue types are cortical bone and muscle/blood.

6. The method of claim 1, wherein the volumetric regions are the whole body section imaged.

7. The method of claim 6, wherein the volumetric regions are each further subdivided into multiple sub-volumetric regions.

8. The method of claim 7, wherein the cross-sectional shapes of the sub-volumetric regions are defined by the cross-sectional margins of the body.

9. The method of claim 1, wherein the volumetric regions are positioned in the posterior region of the body including the spine column and excluding the liver.

10. The method of claim 1, wherein the volumetric regions are positioned automatically.

11. The method of claim 1, wherein the computed anatomical measure is the center-of-mass of spinal bone.

12. The method of claim 1, wherein the representative voxel intensities of the two peaks are the two half-maxima of the peak intensity distributions defined on the outermost sides of the peaks.

13. A computed tomographic (CT) scanner for imaging a patient on a positioning support, the imaging scanner including a plurality of detectors and x-ray source, means to rotate the x-ray source about a center proximal to the patient on the positioning support and means to acquire calibration x-ray attenuation data and determine calibration corrections for the CT images from the calibration attenuation data, the scanner comprising:
   means to acquire the calibration attenuation data from the images of the patient's own tissues without the use of a phantom;
   means to use the attenuation data to compute at least one unique calibration point using measurements from the identified tissue types of the patient; and
   means to calibrate the image voxels in intensity units referenced to the at least one calibration point.

14. The scanner of claim 13, wherein the means to compute at least one calibration point uses known properties of the patients own tissues.

15. The scanner of claim 13, wherein the known properties include the specific gravities of at least one tissue including muscle/blood, fat, air, or cortical bone.

16. The scanner of claim 13, wherein the means to acquire attenuation data includes measurements from the distribution of voxel intensities of the images of the patient.

17. The scanner of claim 16, further including means to compute a calibration point wherein the voxel intensity would be created by substantially equal contributions of two of the tissues.

18. The scanner of claim 13, wherein the means to calibrate image voxels provides a water equivalent calibration of the scanner expressed in Hounsfield units.

19. A method for determining the density of a tissue from CT images of the patient without the use of a reference phantom by computing histograms of the voxel CT numbers of a three dimensional volume of the images that include the tissue and analysis of the histograms to determine the density of the tissue, the method comprising:
finding first one peak of the histogram representing one tissue without manually entering a three dimensional region into a computer;
computing a measure of the peak that does not include determining the mean, mode or standard deviation of the peak;
finding a second peak representative of a second tissue of the histogram without entering a second three dimensional region into a computer;
finding the half-maximum of each histogram peak without operator interaction;
computing a calibration point defined by the voxel intensity value half way between the two found half-maximums;
using a theoretically computed density of the calibration point to calibrate the image voxels to density; and
using the density calibrated voxels to compute the density of the tissue.

20. A method to develop a CT image voxel intensity scale based on density using measured voxel intensities reconstructed by CT scanners, the method including:
computing at least one computed reference density based on known tissue properties;
using the at least one computed reference density to compute new voxel intensities in density units; and
developing a voxel intensity scale (Gram Scale) to analyze and display the tissues of a body using the at least one computed reference density.

21. The method of claim 20, wherein the at least one computed reference density is the computed density of voxels containing equal parts of two tissues.

22. The method of claim 20, wherein the new voxel intensities are calibrated by comparing the measured voxel intensities to the at least one computed reference densities.

23. The method of claim 20, wherein the at least one computed reference density is determined by adding the density of a first tissue to the density of second tissue to obtain a sum and dividing the sum by two.

24. The method of claim 23, wherein the first tissue comprises muscle and the second tissue comprises fat, and wherein the at least one computed reference density is 0.974 $g/cm^3$ and is 26 $mg/cm^3$ less dense than water.

25. The method of claim 20, where the intensity scale (the Gram Scale) has units defined as Gram Units (GU), which are computed by the expression GU=Density $(mg/cm^3)$−1000.

26. The method of claim 25, wherein the Gram Scale defines the voxel intensity of air as −1000 GU, defines the voxel intensity of water as 0 GU, and defines the voxel intensity of cortical bone as +1850 GU.

27. The method of claim 26, wherein the displayed images based on the Gram Scale are subjectively similar to the Hounsfield Scale.

28. A method to automatically calibrate three-dimensional x-ray images for image voxel intensities without using known reference materials in phantoms, the method comprising:
measuring a distribution of the voxel intensities in a volume of the images;
determining a uniquely measured reference point defined as voxels that contain equal contributions of two materials by measurement of voxel distributions of the volume containing the two materials;
computing at least one computed theoretical reference point based on the properties of the two materials; and
using the at least one computed theoretical reference point and the uniquely measured reference point to compute new voxel intensities in the images.

29. The method of claim 28, wherein the x-ray images are created from an x-ray tomosynthesis device.

* * * * *